United States Patent [19]
Schmidt

[11] Patent Number: 5,999,701
[45] Date of Patent: Dec. 7, 1999

[54] ELECTRICAL QUICK-THAWING APPARATUS

[76] Inventor: Günther Schmidt, Bonner Talweg 235, D-53129 Bonn, Germany

[21] Appl. No.: 09/101,140

[22] PCT Filed: Dec. 23, 1996

[86] PCT No.: PCT/DE96/02508

§ 371 Date: Jun. 26, 1998

§ 102(e) Date: Jun. 26, 1998

[87] PCT Pub. No.: WO97/24152

PCT Pub. Date: Jul. 10, 1997

[30]    Foreign Application Priority Data

Dec. 27, 1995  [DE]   Germany .......................... 195 48 826

[51] Int. Cl.⁶ .................................. A61F 7/00; A61M 5/44
[52] U.S. Cl. ........................... 392/470; 219/535; 219/536
[58] Field of Search ............................ 392/470; 219/535, 219/536; 128/DIG. 1; 600/432; A61M 5/44, 1/36

[56]           References Cited

U.S. PATENT DOCUMENTS

| | | |
|---|---|---|
| 3,657,517 | 4/1972 | Hoyt . |
| 4,030,499 | 6/1977 | Bucalo ....................................... 604/51 |
| 4,106,622 | 8/1978 | Windischman .......................... 206/365 |
| 4,731,058 | 3/1988 | Doan ........................................ 604/155 |
| 5,786,572 | 7/1998 | Tonazzi ..................................... 219/523 |
| 5,786,573 | 7/1998 | Fabrikant et al. ....................... 219/535 |

FOREIGN PATENT DOCUMENTS

| | | |
|---|---|---|
| 0282958 | 9/1988 | European Pat. Off. . |
| 0615763 | 9/1994 | European Pat. Off. . |
| 3047784 | 7/1982 | Germany . |
| 3123788 | 1/1983 | Germany . |
| 8236973 | 6/1983 | Germany . |
| 8606622 | 12/1986 | Germany . |
| 3741051 | 6/1989 | Germany . |
| 3940519 | 7/1991 | Germany . |
| 444338 | 2/1968 | Switzerland . |
| 648486 | 3/1985 | Switzerland . |
| 8807384 | 10/1988 | WIPO . |

*Primary Examiner*—Teresa Walberg
*Assistant Examiner*—Thor S. Campbell
*Attorney, Agent, or Firm*—Robert W. Becker & Associates

[57]              ABSTRACT

An electrical quick-thawing apparatus for quickly thawing frozen liquids includes a transmission plate and a clamping and heating device for receiving a container containing a frozen liquid. The clamping and heating device has a heating unit with at least one heating surface and at least one temperature sensor sensing a temperature at the outer wall of the container. An electrical control device including a temperature governor with a control circuit, a set point adjuster, and a switching device controlling heating unit is provided. The output terminal of the temperature sensor is connected to an input terminal of the control circuit. The output terminal of the set point adjuster is connected to an input terminal of the control circuit. The output terminal of the control circuit is connected to the switching device. The switching device controls the heating unit according to signals received from the temperature sensor and the set point adjuster. A highly dynamic linear drive is coupled to the transmission plate and moves transmission plate in a plane. The heating unit is coupled to the transmission plate. The linear drive is embodied as an electromagnetic transducer transforming electrical oscillations into mechanical oscillations at a frequency of 20 to 300 Hz. The electromagnetic transducer has diaphragm moveable in a plane. An oscillation transmission device couples the diaphragm to the transmission plate by a force-locking connection and/or a positive-locking connection.

8 Claims, 3 Drawing Sheets

ELECTRICAL QUICK-THAWING APPARATUS

BACKGROUND OF THE INVENTION

The invention relates to an electrical quick-thawing apparatus for quickly thawing frozen liquids, for example injection or infusion solutions, comprising a transmission plate and a clamping and heating device for receiving a container containing the frozen liquid, especially a syringe or ampule, which clamping and heating device includes an electrical heating unit with at least one heating surface and at least one temperature sensor measuring the temperature at the outer wall of the container. Also included is an electrical control device with a temperature governor whereby the temperature sensor with its output terminal is connected to the temperature governor and with a control circuit which is connected with an outlet terminal to a switching device for controlling the heating unit and controls it depending on signals of the temperature sensor connected to the input terminal of the control circuit and the signals of a set point adjuster.

In clinical practice it is common to administer pharmaceutical products which are supplied by the pharmaceutical industry in standard concentrations and standard volumes and are diluted with carrier solutions to a patient-specific concentration for administration. Since these individually prepared preparations are often used in long-term therapies, the patient-specific active mixture is produced in a respectively large total volume. The individual portions that are to be administered in each session therefore must be filled into syringes or other containers and subsequently frozen.

Only in this manner is it possible to preserve the generally thermally instable active substances over the required time period.

One problem of this accepted and widely used conventional preservation method is that the individual samples require a relatively long thawing time. This is very cumbersome especially when the exact point of time of administration of the ampule volume cannot be exactly predetermined. Even though for the individual patient a time schedule for administering the substance volume is available conventional to first take a blood sample of the patient in order to determine according to the analysis results whether and when the next substance volume is to be administered. This approach thus often results in schedule changes and also in the loss of the already thawed active substance.

In order to avoid this time and cost problem, there is the urgent need to provide a quick-thawing apparatus and a method which allows to thaw the active substance volume quickly.

The prior art discloses microwave thawing devices for frozen liquids which are heated by microwaves of frequencies between 2,425 and 2,475 GHZ. However, these devices have the disadvantage that certain areas of the frozen liquid, due to focusing of the radiation, are overheated so that a uniform heating of the frozen liquid does not take place. The heating of the frozen liquid only in certain areas can result in damage to the ingredients or active substances of the liquid so that chemical modification of the ingredients or the active substances must be assumed. It is apparent that the thawing of infusion solutions or injection solutions in syringes or ampules with conventional microwave thawing devices must be avoided because a chemical modification of the medication as well as denaturation of vaccinations, proteins or serum within the infusion or injection solutions cannot be reliably prevented.

Furthermore, it should be noted that because of the damage of the medically active ingredients of the injection and infusion solutions their medical and therapeutic activity decreases with increasing thawing time. Furthermore, it has been shown that the resulting decrease of medical activity requires a higher dosage and thus a higher concentration of the medically active ingredients in the infusion and injection solutions so that more material must be used, thereby increasing substance use and costs.

Furthermore, the health-detrimental effect of the prior art methods for quickly thawing, such as methods employing microwaves, resulting in hot spot formation, or the use of hot flowing water etc., which may cause modified active substances or contamination with illness-causing microorganisms must be mentioned, whereby their disadvantageous long term effects have been elucidated only partially, but certainly considerable stress on the organism during the decay phase within the patient's body will result.

Also, it has been shown that the use of turntables in microwave thawing devices cannot ensure uniform heating of the frozen injection solutions especially in elongate containers, such as syringes or ampules used widely in the medical field, because, despite the rotation of the turntable causing the container to leave the focusing area, a local overheating of the frozen liquid can be so great that the aforementioned damages of the medication contained in the infusion and injection solutions will occur, i.e., no low-impact thawing will be performed.

Furthermore, the conventional thawing of frozen injection solutions contained in syringes by holding the syringes under hot flowing water, may result in contamination of the liquid by microorganisms which may be forced or introduced by the water jet from the exterior into the gap between the syringe plunger and the syringe body.

The prior art methods for thawing, for example, by heating the active substance volume by using microwave devices, subjecting the syringes to flowing hot water, should therefore be avoided for reasons of thermal instability of the active substances to be administered as well as the lack of required sterile handling of the medium. For these reasons, it is advisable to thaw the ampule at room temperature until thawed resulting however in the great disadvantage of a long thawing time and a need for greater concentration of the active material in the medium because of the expected decomposition of the heat-sensitive active substance.

Moreover, the degree of decomposition of the heat-sensitive active substance can only be estimated and is not exact because the thawing time depends on the actual room temperature which subject to fluctuations so that higher or lower active substance amounts than expected may be administered, a situation which can result in stress to the patient.

Another possibility, e.g., manually heating syringes by one's palm cannot prevent contamination by microorganisms. Furthermore, thawing by hand takes a long time whereby only injection solutions of a volume of 1 ml to 2 ml can be thawed within 5 minutes. However, in hospitals during daily routine work, in emergency rooms or at accidents on site, it is urgently needed and life saving to be able to quickly thaw infusion and injection solutions which are supplied, ready to be administered, in freezers.

Especially manual thawing by the user, which is suitable for only minimal liquid volumes, results in greater time expenditure because the user cannot perform at the same time other activities in hospitals, intensive care units, emergency situations etc., and this results in higher personnel costs.

Since manual thawing of larger amounts of injection solutions to be administered regularly hospitals is very time consuming, especially since the heat capacity of the palm of the user is minimal and the exchange or mixing of cold and warm liquids is time consuming, the conventional methods for thawing as used in hospitals, intensive care units, and emergency rooms are unsuitable and should not be used especially in view of the lack of sterile handling.

It is an object of the present invention to eliminate the aforementioned disadvantages of the prior art. Furthermore, it is desirable to provide a quick thawing apparatus which shortens the thawing time by a multiple and at the same time ensures a careful and sterile treatment of the active substances. Furthermore, it should be possible to provide the quick-thawing apparatus with a simple mechanicdevice in ordertoensure high transportation safety and also minimal maintenance. Also, the quick-thawing apparatus should be embodied such that a quick and sufficient cleaning and sterilization of its components is possible in order to avoid spreading of infection diseases in hospitals.

SUMMARY OF THE INVENTION

The invention resides in an electrical quick-thawing apparatus for quickly thawing frozen liquids, for example, an injection or infusion solution, comprising a transmission plate, a clamping and heating device for receiving a container containing the frozen liquid, especially a syringe, an infusion solution bag or an ampule, which device comprises an electrical heating unit with at least one heating surface and at least one temperature sensor measuring the temperature at the outer wall of the container, as well as an electrical control device with a temperature governor, whereby the temperature sensor is connected with its outlet terminal to a temperature governorwith control circuit, which is connected with its output terminal to a switching device for controlling the heating unit, whereby the switching device controls the heating unit as a function of the signals of the temperature sensor connected to the input terminal of the control circuit and signals of the set point adjuster, characterized in that the transmission plate is coupled to a preferably highly dynamic electrical linear drive or linear direct drive, for example, an electric oscillation drive, and is movable substantially in a plane with a frequency of 20 Hz to 300 Hz, preferably 50 Hz to 200 Hz, and that even more preferred 50 HZ to 100 HZ, and the clamping and heating device can be coupled to the transmission plate.

A further aspect of the invention is a method for quickly thawing frozen liquids with the inventive electric quick thawing apparatus, whereby the temperature governor is a two-point governor, which, when the temperature falls below a set temperature value, supplies a signal, the heating device is switched on only as long as the temperature governor supplies the signal, and the time periods from switching off to switching on the heating unit are evaluated by the switching device as a measure for the thawed state of the liquid, whereby the temperature governorwhen the temperature surpasses a set value will not supply a signal so that the heating unit is switched off.

Highly dynamic in the context of the invention means that the linear drive or the linear direct drive performs movement changes at high frequency, which are in the range of 20 Hz to 300 Hz, preferably 50 Hz to 200 Hz, even more preferred 50 Hz to 100 Hz. A linear direct drive is, for example, a linear drive which is coupled in a force-locking, positive-locking and/or frictional connection via, for example, a linkage to the transmission plate in order to transmit movements.

With the inventive quick-thawing apparatus the thawing action thus is carried out by heat conduction. The cold liquid to be heated within the frozen liquid portion is brought into intimate contact with the hot liquid at high velocity so that the atoms and molecules of the heated liquid portion, which conventionally perform on the average a much faster random movement than the colder liquid, now are forced by the inventive electrical quick-thawing apparatus performing high frequency oscillations to perform orderly movements in the direction toward the frozen liquid portion and transmit their energy upon impact.

The inventive quick-thawing device additionally supports or accelerates the heat convection within the container according to which the heated molecules with extremely high kinetic energy penetrate the surface of the still frozen active substance and thus accelerate heat exchange and thus shorten and drastically the thawing time.

By employing the inventive quick-thawing apparatus the parameters relating to heat transfer are thus supported in a substantially ideal manner, but are also amplified in a sufficient manner such that the thawing period of frozen liquid in contrast to prior art is reduced multiple times, for example, for syringes of a volume of 50 ml with a frozen liquid of also 50 ml it is reduced by about a factor 20.

As containers for the inventive quick-thawing apparatus syringes, ampules, infusion bottles, infusion solution bags etc. can be used. The size, length and design of the clamping and heating device for receiving the container are embodied according to the container to be used. The clamping and heating device, for example, can be tubular or hollow cylindrical for receiving syringes, infusion bottles etc. or, for receiving of infusion solution bags, can be rectangular tub-shaped. The clamping and heating device has a base plate as a support and a heating mantle to be coupled to the base plate which can contact the hollow cylindrical wall of the syringe body, and, for example, can be provided at the outer surface with a thermally insulating cover layer. The base plate can be coupled to the upper side of the transmission plate, for example, by screw connections. The heating mantle can have a hollow cylindrical shape for introduction and receiving of syringe bodies or can be designed according to the shape of other containers to be used.

In one embodiment of the invention, the hollow cylindrical heating mantle has an interior with a central longitudinal axis for receiving a syringe body. The heating mantle in cross-section is concentrically embodied about the central longitudinal axis so that in this design it can be adjusted to and placed about the syringe body. The heating mantle can be open at its forward end, i.e., at its end facing the syringe tip, and its rearward end. Also, the heating mantle can be coupled to the base plate. It is advantageous when the heating mantle is embodied as a heating and thermal insulation mantle. At the side opposite the base plate a gap is provided which extends preferably parallel to the central longitudinal axis of the interior, respectively, the syringe body. The gap compensates the material expansion of the heating mantle and slight diameter differences of the syringe body. The heating mantle can also be shaped so as to match the syringe body whereby the interior of the elastic heating mantle is accessible from above by spreading the free ends of the gap for introducing the syringe body. The syringe body may also be inserted from the rear end into the interior of the heating mantle.

In a further embodiment the heating mantle can comprise two lateral heating mantle halves. They are pivotably coupled to the base plate and can be moved from an open position for receiving the container by pivoting about parallel extending rotational axes into a closed position. In the closed position the lateral heating mantle halves with their heating surface are in intimate contact with the wall of the syringe body. Intimate contact in the context of the invention means that in the closed position an air gap as small as possible exists between the outer wall of the syringe body and the heating surface, respectively, the temperature sensor.

At least two clamping wall halves can be placed about the outer side of the heating mantle or the heating mantle halves facing away from the syringe body. In cross-section the clamping wall halves are concentrically arranged about the central longitudinal axis of the interior, respectively, of the syringe body. Furthermore, between the two pivot joints a heating base mantle with a heating surface may be arranged in order to ensure heat transmission on all sides.

The clamping wall halves are coupled to the base plate. The free upper ends of the clamping wall halves can be coupled with the aid of, for example, a quick locking mechanism such as a latch fastener. It is advantageous in this context when the clamping wall halves upon coupling by the latch fastener are loaded by a pulling force whereby the heating mantle, for example, in a pre-shaped and/or elastic embodiment and/or in the form of two heating mantle halves is forced intimately onto the wall of the syringe body so that an air gap, which would impede heat transfer or temperature measurement, is essentially prevented.

Furthermore, adaptor sleeves of a conventional material with great heat conductivity can be arranged between the syringe body and the heating mantle. They are suitable to transfer heat quickly and to compensate for different diameters of syringes, bottles etc. so that the clamping and heating device can be provided with a uniform diameter.

The heating unit arranged at the inner side of the heating mantle, the lateral heating mantle halves, and the heating base mantle has heating surfaces of conventional heat conducting materials with high specific resistance for converting electrical energy into heat energy. These are known to a person skilled in the art. The heating unit can furthermore be connected to an overheating protection device. The heating surface is preferably connected over its entire surface area to the inner side of the heating mantle with the exception of the area or areas where temperature sensors are arranged so as to be heat-insulated from the heating surface. The embodiment of the inner surfaces so as to provide large surface area contact allows for a fast thawing of frozen liquids such as injection or infusion solutions so that the set value of, for example, maximally 35° C. adjusted by the set point adjuster is efficient in order to substantially reduce the thawing time in comparison to the prior art.

The simple embodiment of the clamping and heating device that is removable from the base plate ensures that a fast and thorough cleaning and sterilization of its parts is possible without having dead spaces where microorganisms could hide and which are difficult to access by the cleaning liquids or steam, a circumstance which must be taken into consideration especially for use of the inventive quick-thawing device in hospitals, emergency rooms, or intensive care units.

The conventional electric linear direct drive or electric linear drive, preferably an oscillation drive, performs highly dynamic reciprocating movements which are substantially within one dimension or plane. The electrical linear direct drive or electrical linear drive can be a conventional shaker or electromechanical transducer with oscillating diaphragm for converting electrical oscillation into mechanical oscillations. For this purpose, an electrical linear drive, linear direct drive or oscillation drive is especially suitable which operates according to the principle of an electrodynamic speaker. It comprises an oscillation coil carrier, a diaphragm, and flexible connecting lines for supplying current to the oscillating coil. The diaphragm arranged on the electrical coil is excited by the oscillations of the coil within a magnetic field and forced to performs oscillations. Preferably, an electrical linear drive, linear direct drive or oscillation drive in the form of a bass speaker can be used in which the oscillating diaphragm surface is of sufficient size and is connected to the transmission plate. In the context of the invention movement or oscillations substantially within a plane mean that deflections within one plane are sufficient in order to ensure heat exchange between the heated liquid areas and the frozen liquid areas. However, it cannot be excluded that the oscillation transmission device could cause deflections of the transmission plate into another plane or that, when using a large diaphragm without sufficient stiffness, partial oscillations or vibrations could occur which possibly overlap the reciprocating movements performed in a plane, whereby these overlapping oscillations, however, can be prevented by guiding the transmission plate in guide rails.

The oscillations or deflections of the diaphragm in a preferred embodiment are received by a oscillation transmitting device and transmitted onto the transmission plate and the base plate coupled to the transmission plate. The diaphragm with the transmission plate can be connected to one another in a form-locking, frictional and/or positive-locking manner. For a positive-locking connection the transmission plate is connected by a linkage or similar connecting components to the diaphragm, respectively, is directly connected to the electrical linear drive or the linear direct drive. The simplest oscillation transmission device is a flange connection or a hollow cylindrical component can be connected by screw connections, welding connections, rivet connections, bolt connections and/or pin connections etc. between the diaphragm and the transmission plate.

In one embodiment of the invention, in which the electrical oscillation drive comprises a diaphragm oscillating in one plane and an oscillation transmission device, the oscillation transmission device may comprise a linkage. The linkage in its simplest embodiment is preferably at least one connecting stay which with one end is centrally connected to the diaphragm and with its other end is coupled to the transmission plate. The mechanical oscillation force of, for example, a bass speaker is sufficient to guide the transmission plate of the inventive quick-thawing apparatus in quick reciprocating movements so that the heat flow of the heated liquid toward the colder liquid is greatly enhanced and the exchange of both liquid areas of different temperatures is thus improved. The heated molecules penetrate with their great kinetic energy into the surface of the frozen active substance and heat the molecules partially so that they are also set in motion.

Due to this exchange there is a heat exchange between the cold, already thawed liquid area and the still frozen liquid area whereby in addition a "bombarding" phenomenon caused by the inventive quick-thawing device, explained in the following, also participates, according to which the frozen liquid is bombarded with heated liquid molecules.

Furthermore, it was noted that with the inventive quick-thawing apparatus the injection solutions in syringes or ampules are heated very gently so that, in contrast to the prior art, a chemical modification, denaturation or other changes of vaccine materials, proteins etc. has not been found. This means that now already prepared and formulated injection liquids ready to be administered can be frozen in syringes and can be thawed in a very short period of time for quick use by a practitioner such as a doctor, nursing personnel etc. especially for routine applications in hospitals.

Especially in emergency situations, larger and already prepared injection solutions containing thermally instable medical substances and having a volume of 20 ml to 100 ml required for maintaining basic biological functions, especially for heart and circulatory problems, can now be provided to the user without requiring time-consuming thawing of these injection liquids or time-consuming mixing of ampule liquids with active substances as well as their introduction into syringes.

The reciprocating movements of the transmission plate coupled to the oscillation drive results in a fast distribution of the heated solution at the inner wall of the syringe body in a direction toward the still frozen solution which is primarily arranged centrally within the syringe. This means that because of the fast reciprocating movement the liquid molecules of the frozen solution are substantially bombarded with liquid molecules of the heated solution. This not only supports the heat transfer from hot to cold but also causes a uniform and homogeneous heating of the frozen injection or infusion solution at its entire still frozen surface. The bombarding with hot liquid molecules effects penetration of these molecules into the frozen liquid so that the frozen liquid is also additionally heated in its interior, and the thawing time is further reduced.

Additionally, it should be noted that in contrast to conventional microwave devices the overheating or hot spot formation in the area of the injection infusion solutions cannot be detected when using the inventive quick-thawing apparatus because only the liquid present at the inner wall of the syringe body is heated and the strong reciprocating movement of the transmission plate results in a combined increased heat conduction and heat convection.

Since in a preferred embodiment the diaphragm of an oscillation drive in the form of an electrodynamic bass speaker is positive-lockingly and force-lockingly connected to the transmission plate of the inventive quick-thawing apparatus, it is ensured with this direct drive of the transmission plate that not only minimal energy oscillation must be provided but also, in contrast to the prior art, only a few movable parts must be provided for generating the oscillation of the transmission plate. Since the number of movable parts for generating the reciprocating movement of the transmission plate is low and the design is very simple, the inventive quick-thawing apparatus requires only minimal maintenance, has a low mechanical failure rate and a long service life.

In a preferred embodiment, the temperature sensor arranged at the inner side of the heating wall of the clamping and heating device measures the temperature of the wall of the syringe body and supplies a signal via lines to the control device. Such control device is a conventional continuous or discontinuous device. The discontinuous control device can comprise a two-point temperature governor whereby two difference values of the set point, i.e., temperature, of preferably 20° C. to 35° C., more preferred 25° C. to 35° C. can be set. The set point adjuster allows setting of the desired value with an operating element such as a turn knob, for example, to temperatures 20° C. to 35° C. The heating current as a set point is switched on and off by a preferably electronic switching device (power on, power off switch).

The temperature governor can switch off the heating current, for example, when the set higher temperature is reached via the control circuit and when the set lower temperature is reached, the current can be switched on. It should be noted that the more liquid has been thawed, the greater the time period between switching off and switching on the heating unit. Accordingly, the heating period, i.e., the partial activation of the heating unit is shorter. The two-point governor, when the temperature falls below the preset value, sends a signal via the control circuit and the switching device so that the heating unit is switched on only as long as the temperature governor supplies the signal. The time period from switching off to switching on the heating unit by the switching device, respectively, the number of non-heating periods can be used as a measure for the thawed state of the liquid. When the set temperature value is surpassed, the temperature governor no longer supplies a signal. The shortening of the time period can be evaluated as a measure for the thawed state of the liquid and can be displayed on a display which is connected to the temperature governor.

In a further embodiment, the heating walls of the clamping and heating device can be textile fabrics provided at their inwardly facing side with heating wires of the heating unit woven into the fabric, whereby the temperature sensor can be placed onto the wall of the syringe body and is heat-insulated and spaced from the heating unit, respectively, its heating surfaces. A key pad which is electrically and controlled techniclogically connected to the control device allows to enter data in regard to the size of the syringe, respectively, the volume of the liquid to be thawed so that in this case the inventive quick-thawing apparatus, base on the increase of the non-heating periods, respectively, of their number, can display the state of the liquid within the syringe.

In a further embodiment, the control device may be a three-point device whereby three different temperature values as set points are used. With the three-point control device two heating units can be inventively employed whereby one heating unit has a greater heating output than the other one. It is possible that the greater heating device is switched on generally all the time to provide the basic load, while the smaller one is additionally switched on depending on the need for heat energy and provides an additional load. This design is advantageous because the change of the control temperature output and the switching on and the switching off periods, respectively, the fluctuations about a desired temperature are reduced.

Because of the uniform heating of the liquid in the area facing the wall of the syringe body and the great increase of heat convection by transport from the hot side to the cold side, the liquid is gently heated at a temperature which will not result in damage of the medically active substances in the injection liquid. Furthermore, it is for the first time possible to use only that much of the medically active substance in the injection liquid as is essentially required by the patient's body because, in contrast to the prior art, the use of the inventive quick-thawing device does not result in decomposition or limitation of the therapeutically effective amount of medication. This also means that in addition to the precisely measurable and therapeutically required amount for a respective administration excess medication is no longer is needed and, furthermore, additional personnel expenditures, required conventionally for a controlled thawing, no longer are needed. These advantages could not be foreseen because the combination of advantages such as quick thawing, reduced damage of therapeutically active substances in the thawed liquids as well as the lack of contamination by microorganisms and thus sufficient guarantee of sterility during the thawing process has been made possible for the first time with the aid of the inventive quick-thawing device in a substantially ideal manner especially for use in hospitals in daily practice as well as in emergency situations.

In a further embodiment, the control circuit for the electrical linear drive, the linear direct drive, the heating device etc., switching devices, temperature sensors, and temperature governors can be connected with the display and/or the key pad electrically and control-techniclogically in a conventional manner. It is possible to display the signals send by the control circuit via a known evaluation device on a display and, if needed, to display the increase of the time period between switching off and switching on of the heating unit as a measure for the thawed state of the liquid.

BRIEF DESCRIPTION OF THE DRAWINGS

Specific Embodiments

Further details, aspects and advantages of the invention result from the following description with reference to the drawings. It is shown in a simplified and schematical manner in an enlarged scale, without being true to scale, in FIG. 1 a longitudinal section of a clamping and heating device of the inventive quick-thawing apparatus.

DESCRIPTION OF PREFERRED EMBODIMENTS

Figure 1:
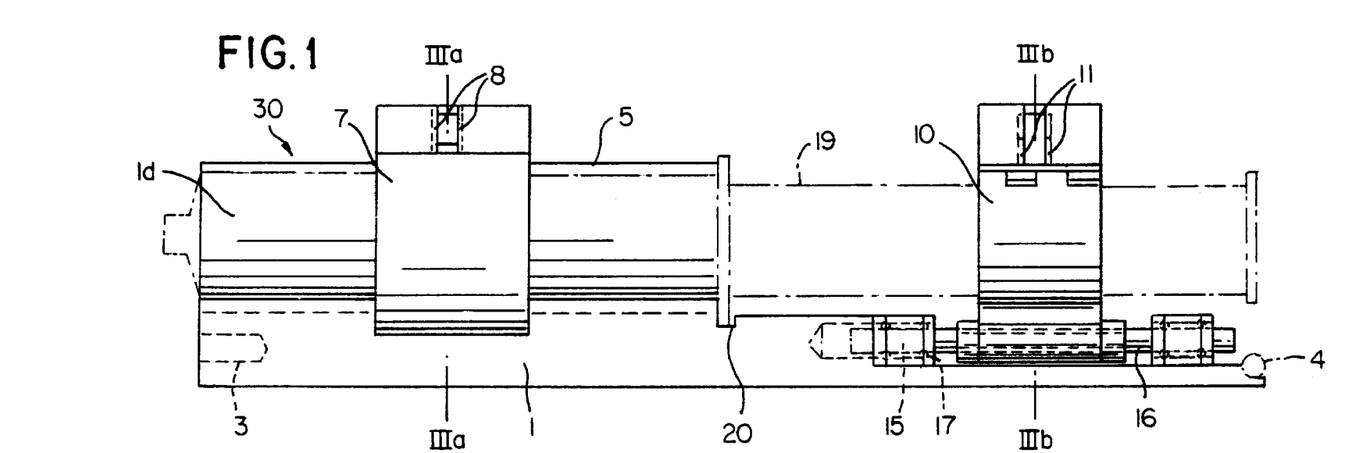
Figure 2:
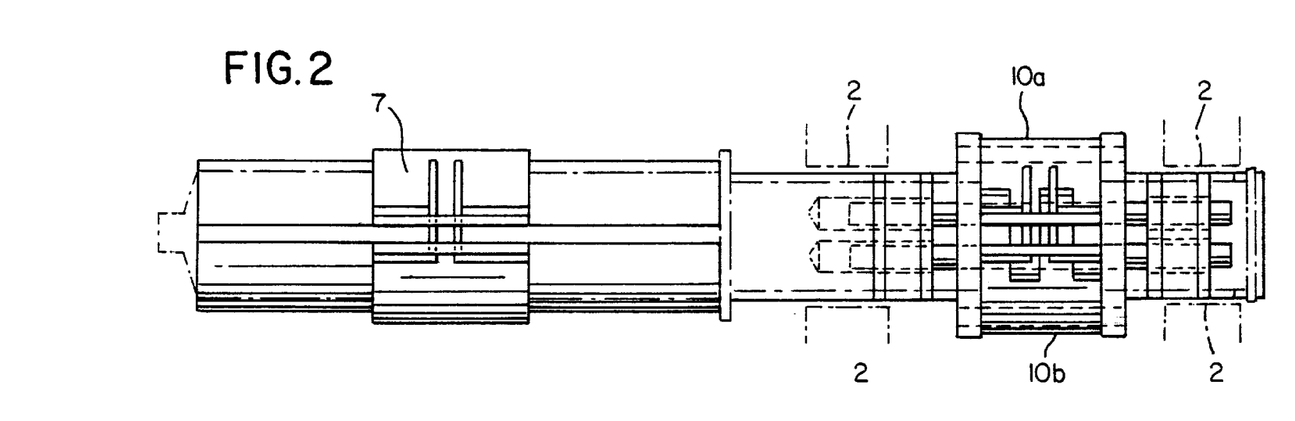
FIG. 2 a plan view onto the clamping and heating device of the inventive quick-thawing apparatus.
Figure 3A:
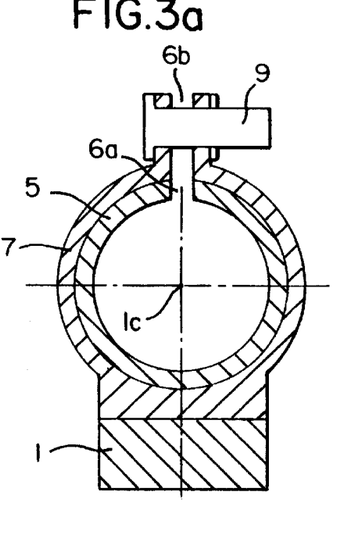
FIG. 3 a view of section A–B and of section C–D according to FIG. 1.
Figure 3B:
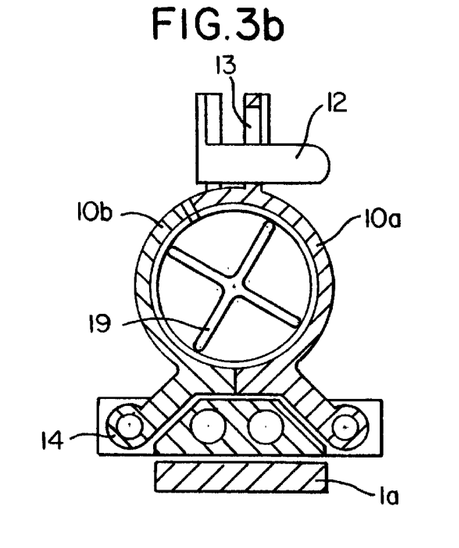

On the transmission plate $1a$ a base plate 1 which is connected by quick-connect devices, i.e., clamping closures 3,4 (or alternatively connecting screws or clamps) to the transmission plate $1a$. The clamping and heating device 30 is a hollow cylinder which has a heating and thermal insulation mantle 5 with an upper gap $6a$ for compensating dimensional deviations resulting from heating or from different syringe body diameter. The free ends of the heating and thermal insulation mantle 5 opposite the gap $6a$ can be spread substantially tangentially (open position) in order to be able to introduce the syringe with syringe body $1d$ in the longitudinal direction. The side of the heating and thermal insulation mantle 5 facing the interior is provided with heating units with heating surfaces not shown in the drawing. The size and thus the diameter of the heating and thermal insulation mantle 5 corresponds substantially to the conventional standard of outer diameters of syringe bodies $1d$ of a respective syringe size of 50 ml volume. Two clamping wall halves 7 are concentrically placed about the heating and thermal insulation mantle 5. They are fixedly connected at the base of the base plate 1. At the upper side opposite the base plate 1 the free ends of the clamping wall halves 7 are positioned and form a second gap $6b$ where clamping latch fasteners 9 are arranged. (FIGS. 1 through 3).

In the open position of the latch fasteners 9 the syringe with its syringe body $1d$ can be introduced into the interior of the heating and thermal insulation mantle 5. In the closed position of the latch fasteners 8, 9 (latch 9, latch closure with toothing 8, to be opened by compression of the two latches 9) the clamping wall halves 7 which are elastic or tension-elastic are loaded such that the heating and thermal insulation mantle 5 comes into intimate contact at the syringe body $1d$ so that no considerable air gap remains which would impede heat transfer and heat measurement.

In order to prevent a displacement of the plunger 19 of the syringe, for example, in the longitudinal direction of the syringe body $1d$ caused by the reciprocating movement during the thawing process, the syringe plunger 19 is also secured by clamping halves 10 (right clamping half $10a$ left clamping half $10b$) which are secured by latch fasteners 11, for example, including a toothing. Opening is carried out by compression of the two latches (latch 12, latch through opening 13) by applying a clamping force for bringing them into the closed positioned. The clamping halves 10 can be pivotably coupled (not shown) by pivot joints at the base plate 1. The pivot joints 14 can be arranged at the upper side of the base plate 1 and can also be slidably adjustable in the longitudinal direction parallel to the central longitudinal axis $1c$ of the syringe body $1d$ on the base plate 1. The movability of the pivot joints 14 is possible by slide bearings 15 whereby guide rods 16 can be through the slide bearings 15 parallel to the central longitudinal axis $1c$ of the syringe body $1d$. The pivot joints 14 are coupled to the guide rods 16 and the guide rod 16 are adjustable in the slide bearings 15 by adjusting screws at the base plate 1. Rubber rings 17 serve as buffers for dampening the slide bearing. Adjustable lateral guides 2 on the transmission plate $1a$ serve for facilitating introduction of the clamping and heating device 30. An outwardly projecting edge of the syringe body $1d$ engages a groove 20 in the base plate 1 so that the syringe body $1d$ is secured in the longitudinal direction.

Figure 4:
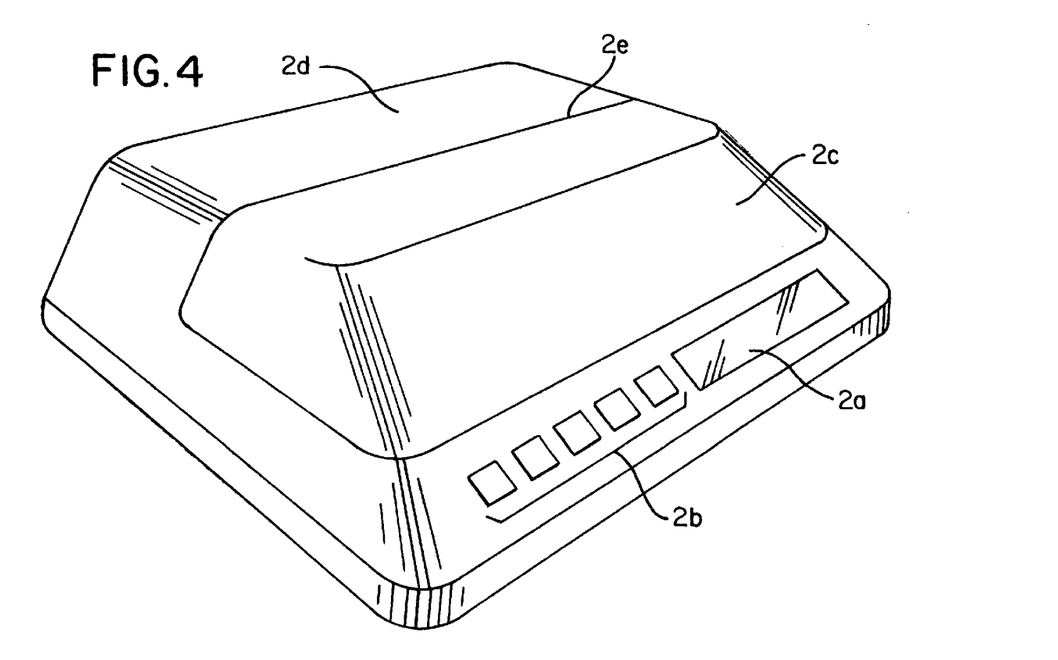
FIG. 4 a perspective view of the inventive quick-thawing apparatus.

At the inner side of the heating and thermal insulation mantle 5 a temperature sensor (not shown) is positioned so as to be spaced from the heating unit and so as to be heat insulated therefrom. It emits a signal via lines to an electrical two-point control device whose output terminal is connected to the temperature governor of the electric two-point control device. The control circuit of the electrical two-point control device provides at its output terminal a comparative value of the temperature detected by the temperature sensor at the syringe body with the set point value provided via the key pad $2b$ that via the switching device (power on, power off) provides the connection to the heating unit, respectively, interrupts it. At the same time, a signal from the control device is supplied to the switching circuit (power on and off) of the electrical oscillation drive. A current supply supplies current to the electrical two-point control device with a control circuit and the display $2a$ connected to the temperature governor. The control circuit is connected with its input terminal to the temperature sensor and the set point adjuster which can be adjusted via the key pad $2b$ by keys or a turn knob. The current supply also supplies current to a switching device for the heating device connected to the outlet terminal of the control circuit and to the electrical oscillation drive as well as to the display 2a also connected to the output terminal of the control circuit. The display 2 is, for example, formed by LEDs or LCDs (FIG. 4).

The electrical oscillation drive is embodied in principle as a bass speaker whereby the transmission plate 1a is positive-lockingly and force-lockingly connected by a linkage to the diaphragm.

Comparative tests have shown for a control temperature at the syringe surface between 25° C. to 35° C., when using a 50 ml syringe with 50 ml frozen liquid, that the time period for reaching the thawed state of the liquid can be reduced by a factor 20 in comparison to the prior art whereby as a control a syringe of identical size and liquid volume is heated with normal convection. Furthermore, it should be noted that in the control example additional time was needed for the user to adjust the water temperature to lukewarm, which has not been taken into consideration in the results of the comparative tests. Also not considered was the different sensing abilities of different users to adjust lukewarm water so that in the prior art it is not ensured that injection liquids are always exposed to the same temperature by different users.

The clamping and heating device coupled to the upper side of the transmission plate 1a, if needed, can be covered by a safety closure 2c which is coupled by pivot joints 2e at the rear of the housing 2d to the inventive quick-thawing device.

Figure 5:
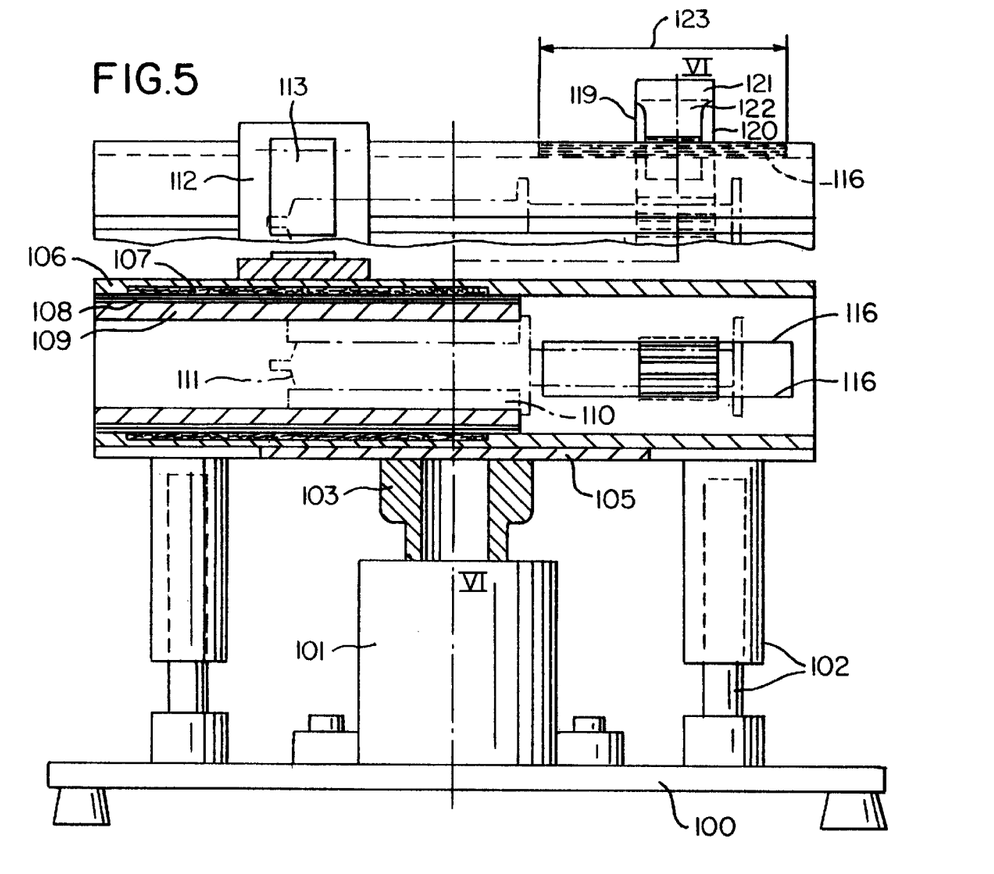
FIG. 5 a longitudinal section and a plan view of a clamping and heating device of the inventive quick-thawing device with a oscillation transmission device coupled to a linear drive which transmission device is connected to a transmission plate.

In FIG. 5 the oscillation transmission device is embodied as a hollow cylindrical component 103 coupled to the diaphragm of a linear drive in a form locking and force-locking manner. The linear drive is also called a linear direct drive because of its mechanical positive-locking and positive-locking coupling. The linear drive operates according to the principle of an electro-dynamic speaker with reciprocating movement substantially in the direction, for example, of the X axis of the oscillating diaphragm. Linear drives are known in the prior art, and a conventional one is shown in the drawing. The linear drive is positioned in a hollow cylindrical housing 101 with upper opening. From the opening the component 103 projects and is positive-lockingly and force-lockingly coupled to the transmission plate 105. The vibrations or oscillations of the diaphragm are transmitted by the component 103 to the transmission plate 105. The transmission plate 105 is provided laterally with at least two guide columns or rails 102 positioned on the base plate 100 in order to provide reciprocating movement primarily in the X direction. The clamping and heating device comprises a thermally insulating layer 107 which surrounds a heating wall 108 with heating unit and heating surfaces facing the interior.

Metal sleeves 109 with sufficient heat conductivity are arranged on the side of the heating wall 108 facing the interior. Adaptor sleeves 110 also having great heat conductivity can also be provided if the diameter of the syringe body 111 to be received in the interior is so small that the metal sleeve 109 does not contact sufficiently the wall of the syringe body 111 but is spaced therefrom. Any material with great thermal conductivity is suitable as a metal sleeve 109 and adaptor sleeve 110, and such materials are known to a person skilled in the art. Reference number 112 (clamping device) and 113 (clamping/closure latch) are representative for the aforementioned clamping latch closure, respectively its parts. The clamping housing 106 corresponds substantially to the aforementioned clamping wall halves 7.

Figure 6:
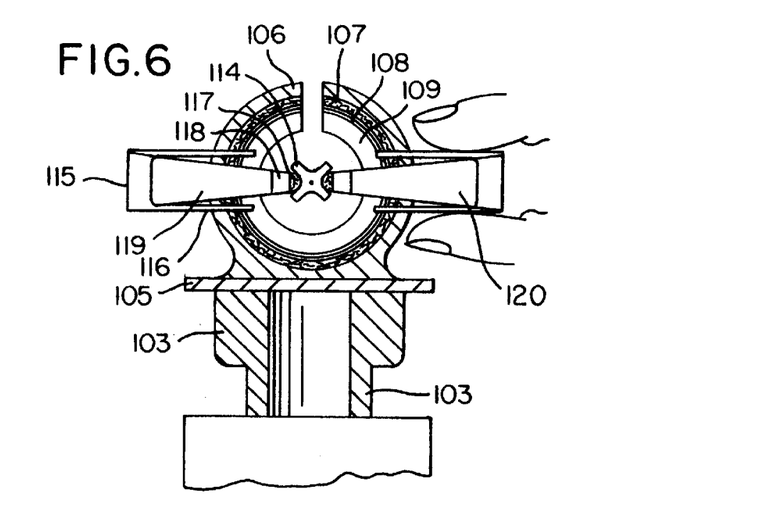
FIG. 6 a section with an end view of the section A–B of FIG. 5.

The piston rod or plunger 114 (FIG. 6) of the syringe is guided in a clamping device 115. The clamping device serves to provide a vibration-free support of the syringe plunger 114 in the vertical direction. The clamping device 115 also is entrained with the translatory movements which result by volume reduction upon heating, from the frozen state of the liquid with active substance up to 4° C. and the subsequent volume increase due to further heating of the liquid with active substance from 4° C. to 35° C. The conventional clamping device 115 comprises two laterally arranged leaf springs 119 and 120. Upon heat expansion, the leaf springs 119, 120 bent slightly in the longitudinal direction, but they remain stiff in the vertical direction. The clamping device 115 also has securing springs 122 at the upper and lower side which engage at the upper and lower side a toothing 116. At the free end of the leaf springs 119, 120 rubber stops 117 are arranged which allow sufficient contact and guiding of the leaf springs 119, 120 at the plunger 114. As a function of the size of the plunger 114 the clamping device 115 can be adjusted with an adjusting range 123. Upper and lower metal parts 118, 121 serve for fastening these leaf springs 119, 120. The upper metal piece 121 serves in addition for fastening the securing spring 122.

Furthermore, it was shown that rapid shaking of the syringe under flowing hot water would result in a movement of the plunger 19 parallel to the central longitudinal axis 1c of the syringe body which could cause ejection of the injection liquid or aspiration of microorganisms into the gap between the plunger 19 and the inner wall of the syringe body 1d or via the opening of the syringe. In contrast, the inventive quick-thawing apparatus not only provides a very short thawing time but also ensures sufficiently that thawing is carried out under sterile conditions upon heating of the frozen liquid to a temperature which corresponds to the desired temperature, preferably body temperature. This perimeter of adjustability of the liquid to be thawed to body temperature is also necessary with regard to medical considerations because patients will experience the injection of liquids that are not at body temperature as uncomfortable or bothersome.

Thus, the inventive quick-thawing device is a quickly operating, gentle, and personnel-saving device which due to its simple mechanical design can be quickly cleaned or disinfected, requires little maintenance, and is reliable.

The present invention is, of course, in no way restricted to the specific disclosure of the specification and drawings, but also encompasses any modifications within the scope of the appended claims.

What is claimed is:

1. An electrical quick-thawing apparatus for quickly thawing frozen liquids, said apparatus comprising:
   a transmission plate;
   a clamping and heating device for receiving a container containing a frozen liquid;
   said clamping and heating device including a heating unit with at least one heating surface and at least one temperature sensor sensing a temperature at an outer wall of the container;

an electrical control device including a temperature governor with a control circuit, a set point adjuster, and a switching device controlling said heating unit;

said temperature sensor having an output terminal connected to an input terminal of said control circuit;

said set point adjuster having an output terminal connected to an input terminal of said control circuit;

said control circuit having an output terminal connected to said switching device;

said switching device controlling said heating unit according to signals received from said temperature sensor and said set point adjuster;

a highly dynamic linear drive coupled to said transmission plate and moving said transmission plate in a plane;

said heating unit coupled to said transmission plate;

said linear drive embodied as an electromagnetic transducer transforming electrical oscillations into mechanical oscillations at a frequency of 20 to 300 Hz;

said electromagnetic transducer comprising a diaphragm moveable in a plane;

an oscillation transmission device coupling said diaphragm to said transmission plate by a force-locking connection, a positive-locking connection, or a force-locking and positive-locking connection.

2. An apparatus according to claim 1, wherein said oscillation transmission device is a flange connection.

3. An apparatus according to claim 1, wherein said oscillation transmission device is comprised of at least one connecting stay having a first and a second end, wherein aid first end is fastened centrally to said diaphragm and wherein said second end is fastened to said transmission plate.

4. An apparatus according to claim 1, wherein said linear drive is a bass speaker.

5. An apparatus according to claim 1, wherein said clamping and heating device comprises a base plate detachable connected to said transmission plate by quick connect devices.

6. An apparatus according to claim 1, wherein said transmission plate has at least two lateral guide rails connected to said base plate and allowing a reciprocating movement of said transmission plate relative to said base plate.

7. An apparatus according to claim 1, wherein said temperature sensor is positioned at least on one wall of said container in intimate contact.

8. An apparatus according to claim 1, wherein said clamping and heating device comprises a hollow cylindrical heating mantle.

* * * * *